United States Patent [19]

Evans et al.

[11] 4,161,592

[45] Jul. 17, 1979

[54] PIPERIDINYL-s-TRIAZINES

[75] Inventors: Samuel Evans, Basel; Michael Rasberger, Riehen, both of Switzerland

[73] Assignee: Ciba-Geigy Corporation, Ardsley, N.Y.

[21] Appl. No.: 812,294

[22] Filed: Jul. 1, 1977

[30] Foreign Application Priority Data

Jul. 8, 1976 [CH] Switzerland .................. 8774/76

[51] Int. Cl.$^2$ ................. C07D 251/46; C07D 251/52; C07D 251/70

[52] U.S. Cl. ................. 544/198; 544/209; 544/212; 544/219; 544/214; 544/195; 210/45.8 NT

[58] Field of Search ............... 544/219, 214, 212, 209, 544/198, 195

[56] References Cited

U.S. PATENT DOCUMENTS

| | | | |
|---|---|---|---|
| 2,725,379 | 11/1955 | Bernstein et al. | 544/209 |
| 3,265,690 | 8/1966 | Matter et al. | 544/212 |
| 3,925,376 | 12/1975 | Chalmers et al. | 544/219 |
| 4,008,829 | 8/1977 | Cassandrini et al. | 544/198 |
| 4,042,562 | 8/1977 | Hofer et al. | 544/209 |
| 4,086,204 | 4/1978 | Cassandrini et al. | 544/198 |

*Primary Examiner*—John M. Ford
*Attorney, Agent, or Firm*—Wenderoth, Lind & Ponack

[57] ABSTRACT

New 1,3,5-triazines containing at least one hindered phenolic moiety and at least one hindered amine moiety are useful light stabilizers and antioxidants for polymeric materials.

9 Claims, No Drawings

PIPERIDINYL-s-TRIAZINES

The present invention relates to new substituted 1,3,5-triazines, their manufacture, their use for stabilising organic material and to the organic material protected, with the aid thereof, against oxidative and light-induced degradation.

The use of piperidine derivatives of 1,3-pyrimidine and 1,3,5-triazine as a light stabiliser is known from British Patent Specification No. 1,393,551. Furthermore, phenolic 1,3,5-triazines which are suitable for use as antioxidants are known from U.S. Pat. No. 3,255,191.

A new class of 1,3-pyrimidines and 1,3,5-triazines, which combines a light stabilising effect and surprisingly good antioxidative properties in one and the same molecule, has now been found. Moreover, the new compounds are distinguished by good colour properties.

The invention relates to new compounds corresponding to the general formula I

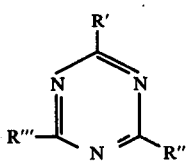

(I)

or to addition salts thereof, in which one of the radicals R', R" and R''' denotes a group of the formula II:

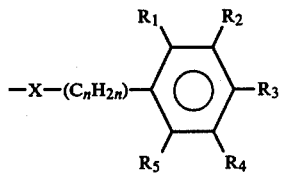

(II)

wherein one of $R_1$ and $R_3$ is —OH and the other is hydrogen, $R_2$ denotes $C_1$-$C_{12}$ alkyl, $C_5$-$C_7$ cycloalkyl, $C_6$-$C_{10}$ aryl or $C_7$-$C_9$ aralkyl, $R_4$ and $R_5$ are hydrogen, $C_1$-$C_{12}$ alkyl, $C_5$-$C_7$ cycloalkyl, $C_6$-$C_{10}$ aryl or $C_7$-$C_9$ aralkyl, n denotes 0 to 12 and X denotes —O—, —S— or —NR$_6$— wherein $R_6$ is hydrogen or $C_1$-$C_{12}$ alkyl, and one of the radicals R', R" and R''' denotes one of the groups

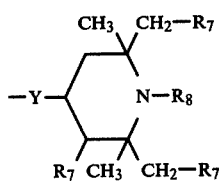

(III)

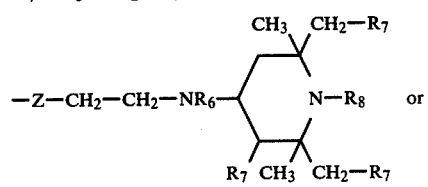

(IV)

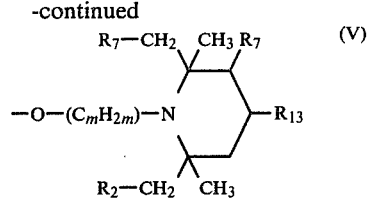

(V)

in which Y is —O— or —NR$_6$— wherein $R_6$ has the meaning defined above, Z denotes —O— or —S—, m is 1 to 6, $R_7$ is hydrogen or $C_1$-$C_8$ alkyl and $R_8$ is hydrogen, oxyl, $C_1$-$C_{12}$ alkyl, $C_3$-$C_6$ alkenyl, $C_3$-$C_4$ alkinyl, $C_2$-$C_{21}$ alkoxyalkyl, $C_7$-$C_9$ aralkyl, 2,3-epoxypropyl, an aliphatic acyl group with 1-4 C atoms or one of the groups —CH$_2$COOR$_9$, —CH$_2$—CH(R$_{10}$)—OR$_{11}$, —COOR$_{12}$ or —CONHR$_{12}$, wherein $R_9$ is $C_1$-$C_{12}$ alkyl, $C_3$-$C_6$ alkenyl, phenyl, $C_7$-$C_8$ aralkyl or cyclohexyl, $R_{10}$ is hydrogen, methyl or phenyl, $R_{11}$ denotes hydrogen, an aliphatic, aromatic, araliphatic or alicyclic acyl group with 1-18 C atoms, wherein the aromatic part, if appropriate, can be substituted by chlorine, $C_1$-$C_4$ alkyl, $C_1$-$C_8$ alkoxy and/or by hydroxyl, and $R_{12}$ denotes $C_1$-$C_{12}$ alkyl, cyclohexyl, phenyl or benzyl, and $R_{13}$ denotes hydrogen, —OH or one of the groups —O—CO—R$_{14}$ or —NR$_{12}$—CO—R$_{14}$, wherein $R_{14}$ denotes $C_1$-$C_{12}$ alkyl or phenyl, and one of the radicals R', R" and R''' independently of the others denotes an identical or different group of the formula II, or denotes an identical or different group III, IV or V, or denotes —N$_3$ or one of the groups —S—R$_{15}$, —OR$_{17}$, —P(O)—(OR$_{17}$)$_2$ or —NR$_{18}$R$_{19}$, wherein $R_{15}$ denotes hydrogen, $C_1$-$C_{18}$ alkyl, $C_5$-$C_7$ cycloalkyl, $C_6$-$C_{10}$ aryl, $C_7$-$C_9$ aralkyl or the group —(C$_p$H$_{2p}$)—CO—OR$_{16}$ wherein $R_{16}$ is $C_1$-$C_{18}$ alkyl and p denotes 1 to 6, $R_{17}$ denotes $C_1$-$C_{18}$ alkyl, $C_6$-$C_{10}$ aryl or $C_7$-$C_9$ aralkyl and $R_{18}$ and $R_{19}$ independently of one another denote hydrogen, $C_1$-$C_{18}$ alkyl, $C_5$-$C_7$ cycloalkyl, $C_6$-$C_{10}$ aryl, $C_7$-$C_9$ aralkyl or the group

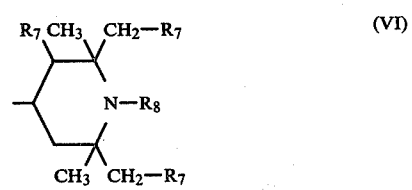

(VI)

in which $R_7$ and $R_8$ have the meaning defined above.

As branched or unbranched $C_1$-$C_{12}$ alkyl, $R_2$, $R_4$ and $R_5$ can be, for example, methyl, ethyl, isopropyl, sec.-butyl, tert.-butyl, amyl, n-hexyl, 1,1,3,3-tetramethylbutyl, tert.-nonyl, n-decyl or n-dodcecyl. Alkyl groups with 1-8 C atoms and especially those with 1-4 C atoms are preferred as $R_2$ and $R_4$. Alkyl groups with 1-6 C atoms and especially methyl are preferred as $R_5$.

Examples of $R_2$, $R_4$ and $R_5$ as $C_5$-$C_7$ cycloalkyl are cyclopentyl, methylcyclopentyl, cyclohexyl or methylcyclohexyl.

Examples of $R_2$, $R_4$ and $R_5$ as $C_6$-$C_{10}$ aryl are phenyl, α-naphthyl or β-naphthyl, especially phenyl.

Examples of $R_2$, $R_4$ and $R_5$ as $C_7$-$C_9$ aralkyl are benzyl, α-phenyl-ethyl or 2-phenyl-propyl, especially benzyl.

Examples of $R_6$ as $C_1$-$C_{12}$ alkyl are methyl, ethyl, n-butyl, n-hexyl, n-octyl, n-decyl or n-dodecyl. Preferably, $R_6$ is an alkyl group with 1 to 4 C atoms. However, the particularly preferred meaning of $R_6$ is hydrogen.

Examples of $R_7$ as $C_1$-$C_8$ alkyl are methyl, ethyl, isopropyl, n-butyl, amyl, n-hexyl or n-octyl. Alkyl groups with 1-4 C atoms, and especially ethyl and methyl, are preferred. Compounds in which $R_7$ denotes methyl or hydrogen are to be singled out in particular.

Examples of $R_8$ as $C_1$-$C_{12}$ alkyl are methyl, ethyl, n-propyl, n-butyl, n-pentyl, n-hexyl, n-octyl, n-decyl or n-dodecyl, with alkyl groups with 1-8 C atoms, in particular those with 1-4 C atoms and above all methyl, being preferred; or $R_8$ is preferably hydrogen.

Examples of $R_8$ as $C_3$-$C_6$ alkenyl are allyl, 2-butenyl or 2-hexenyl, especially allyl.

An example of $R_8$ as $C_3$-$C_4$ alkinyl is propargyl.

If $R_8$ denotes $C_2$-$C_{21}$ alkoxyalkyl, the alkyl part can contain 1-3 C atoms and the alkoxy part can consist of 1-18 C atoms, such as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl, and compounds in which $R_8$ denotes an alkoxy group with 2-6 C atoms should be especially mentioned.

Examples of $R_8$ as $C_7$-$C_9$ aralkyl are benzyl, $\alpha$-phenyl-ethyl or $\alpha,\alpha$-dimethylbenzyl.

Examples of $R_8$ as an aliphatic acyl group with 1-4 C atoms are formyl, acetyl, acryloyl or crotonyl, especially acetyl.

If $R_8$ is the group —$CH_2COOR_9$, $R_9$ as $C_1$-$C_{12}$ alkyl denotes, for example, methyl, ethyl, isopropyl, n-butyl, isobutyl, t-butyl, isopentyl, n-octyl, n-decyl or n-dodecyl. Preferably $R_9$ is $C_1$-$C_4$ alkyl, and examples of $R_9$ as $C_3$-$C_6$ alkenyl are allyl, 2-butenyl or 2-hexenyl. Examples of $R_9$ as $C_7$-$C_8$ aralkyl are benzyl or $\alpha$-phenylethyl.

If $R_8$ is the group —$CH_2$—$CH(R_{10})$—$OR_{11}$, $R_{10}$ denotes hydrogen, methyl or phenyl, especially hydrogen. Examples of $R_{11}$ as an aliphatic, aromatic, alicyclic or araliphatic $C_1$-$C_{18}$ acyl radical which is substituted in the aromatic part, if appropriate, by chlorine, $C_1$-$C_4$ alkyl, such as methyl, ethyl, n-propyl or t-butyl, or by $C_1$-$C_8$ alkoxy, such as methoxy, ethoxy, butoxy or octoxy, and/or by hydroxyl, are acetyl, propionyl, butyroyl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, $\beta$-(3,5-di-t-butyl-4-hydroxyphenyl)-propionyl, phenylacetyl, cinnamoyl, or hexahydrobenzoyl.

If $R_8$ is the group —$COOR_{12}$, examples of $R_{12}$ as $C_1$-$C_{12}$ alkyl are methyl, ethyl, isobutyl, n-hexyl, n-octyl, n-decyl or n-dodecyl. Alkyl groups with 1-4 C atoms are preferred as $R_{12}$.

Y is —O— or —$NR_6$—, preferably

Z denotes —O— or —S—, preferably —O—, and examples of $R_{14}$ as $C_1$-$C_{12}$ alkyl are methyl, ethyl, n-butyl, n-hexyl, n-octyl, n-decyl or n-dodecyl.

Examples of $R_{15}$, $R_{16}$, $R_{18}$ and $R_{19}$ as $C_1$-$C_{18}$ alkyl are methyl, ethyl, isopropyl, n-butyl, n-pentyl, n-hexyl, n-octyl, n-decyl, n-dodecyl, n-tetradecyl, n-hexadecyl or n-octadecyl; preferably $R_{15}$ and $R_{19}$ are an alkyl group with 1 to 12 C atoms, especially an alkyl group with 8 C atoms or hydrogen.

Examples of $R_{15}$, $R_{18}$ and $R_{19}$ as $C_5$-$C_7$ cycloalkyl are cyclopentyl, methylcyclopentyl, cyclohexyl or methylcyclohexyl, and preferably cyclohexyl.

Examples of $R_{15}$, $R_{18}$ and $R_{19}$ as $C_6$-$C_{10}$ aryl are phenyl, $\alpha$-naphthyl or $\beta$-naphthyl, especially phenyl.

Examples of $R_{15}$, $R_{18}$ and $R_{19}$ as $C_7$-$C_9$ aralkyl are benzyl, $\alpha$-ethylphenyl or $\alpha,\alpha$-dimethylbenzyl.

Examples of $R_{17}$ as $C_1$-$C_{18}$ alkyl are methyl, ethyl, isopropyl, n-butyl, sec.butyl, t-butyl, amyl, n-hexyl, n-octyl, n-decyl, n-dodecyl, n-tetradecyl, n-hexadecyl or n-octadecyl. Preferably, $R_{17}$ is an alkyl group with 1 to 12, and especially with 1 to 4, C atoms. Ethyl, propyl or butyl is very particularly preferred as $R_{17}$.

Examples of $R_{17}$ as $C_6$-$C_{10}$ aryl are phenyl, $\alpha$-naphthyl or $\beta$-naphthyl, and especially phenyl.

Examples of $R_{17}$ as $C_7$-$C_9$ aralkyl are benzyl, $\alpha$-ethylphenyl or $\alpha,\alpha$-dimethylbenzyl.

Salts which may be mentioned of the compounds are especially acid addition salts with inorganic or organic acids. The salts can be obtained in the customary manner and the free bases which in turn are preferred can be recovered from the salts. Acids which are suitable for forming salts are in particular inorganic acids, such as hydrochloric acid, sulphuric acid and phosphoric acid but also an organic acid, such as, for example, p-toluenesulphonic acid.

Those compounds of the formula I are preferred, in which one of the radicals R', R" and R''' is a group of the formula II wherein $R_1$ is hydrogen, $R_2$ denotes $C_1$-$C_{12}$ alkyl, $R_3$ is —OH, $R_4$ is hydrogen or $C_1$-$C_{12}$ alkyl, $R_5$ denotes hydrogen or $C_1$-$C_6$ alkyl, n is 0 to 6 and X denotes —O—, —S— or —$NR_6$— wherein $R_6$ is hydrogen or $C_1$—$C_4$ alkyl, and one of the radicals R', R" and R''' denotes one of the groups of the formula III or V, in which m denotes 2, Y is —O— or —$NR_6$—, $R_7$ is hydrogen or $C_1$-$C_4$ alkyl and $R_8$ is hydrogen, oxyl, $C_1$-$C_8$ alkyl, $C_3$-$C_4$ alkenyl or alkinyl, $C_2$-$C_6$ alkoxyalkyl, $C_7$-$C_9$ aralkyl, acetyl, acryloyl or crotonoyl or one of the groups —$CH_2$—$COOR_9$, —$CH_2$—$CH(R_{10})$—$OR_{11}$, —$COOR_{12}$ or —$CONHR_{12}$, wherein $R_9$ is $C_1$-$C_4$ alkyl, $C_3$-$C_4$ alkenyl, phenyl, $C_7$-$C_8$ aralkyl or cyclohexyl, $R_{10}$ is hydrogen, methyl or phenyl, $R_{11}$ denotes hydrogen or an aliphatic, aromatic, alicyclic or araliphatic acyl group with 1-18 C atoms, wherein the aromatic part, if appropriate, can be substituted by chlorine, $C_1$-$C_4$ alkyl, $C_1$-$C_8$ alkoxy and/or hydroxyl, $R_{12}$ is $C_1$-$C_{12}$ alkyl and $R_{13}$ denotes hydrogen, —OH or one of the groups —O—CO—$R_{14}$ or —NH—CO—$R_{14}$, wherein $R_{14}$ denotes $C_1$-$C_{12}$ alkyl, and one of the radicals R', R" and R''' independently of the others denotes an identical or different group of the formula II, wherein the substituents have the meaning defined above, or denotes an identical or different group III or V, wherein the substituents have the meaning defined above, or denote —$N_3$ or Cl or one of the groups —S—$R_{15}$, —$OR_{17}$, —$P(OR_{17})_2$ or —$NR_{18}R_{19}$, wherein $R_{15}$ denotes hydrogen, $C_1$-$C_{18}$ alkyl or the group —$(C_pH_{2p})$—CO—$OR_{16}$ wherein $R_{16}$ denotes $C_1$-$C_{18}$ alkyl and p is 1 to 4, $R_{17}$ is $C_1$-$C_{12}$ alkyl and $R_{18}$ and $R_{19}$ independently of one another denote hydrogen, $C_1$-$C_{12}$ alkyl, phenyl or a group of the formula VI.

Those compounds of the formula I are particularly preferred, in which R' is a group of the formula II wherein $R_1$ denotes hydrogen, $R_2$ denotes $C_1$-$C_8$ alkyl, $R_3$ is —OH, $R_4$ denotes hydrogen or $C_1$-$C_4$ alkyl, $R_5$ is hydrogen or methyl, n is 0 to 5 and X denotes —NH—, and R" denotes one of the groups of the formula III or V, wherein m denotes 2, Y is —NH—, $R_7$ denotes hydrogen or methyl and $R_8$ is hydrogen, $C_1$–$C_4$ alkyl, or, acetyl, and $R_{13}$ denotes hydrogen or —OH, and R''' is identical to or different from R' and denotes a group of the formula II in which the substituents have the meaning defined above or R''' is identical to or different from R'' and denotes one of the groups III or V in which the substituents have the meaning defined above, or denotes —$N_3$, or one of the radicals —S—$R_{15}$, —O—$R_{17}$, —P(O)—(O$R_{17}$)$_2$ or —NH$R_{19}$, wherein $R_{15}$ denotes $C_1$–$C_{12}$ alkyl or the group —($C_pH_{2p}$)—CO—O$R_{16}$ wherein $R_{16}$ is $C_1$–$C_2$ alkyl and n is 1 to 5, $R_{17}$ denotes $C_1$–$C_2$ alkyl and $R_{19}$ denotes a group of the formula VI; and especially those compounds of the formula I in which R' is a group of the formula II wherein $R_1$ is hydrogen, $R_2$ is $C_1$–$C_4$ alkyl, $R_3$ is —OH, $R_4$ denotes hydrogen or $C_1$–$C_4$ alkyl, $R_5$ denotes hydrogen or methyl, n is 0 to 5 and X denotes —NH—, and R'' denotes one of the groups of the formula III or V wherein Y is —NH—, m is 2, $R_7$ denotes hydrogen, $R_8$ denotes hydrogen, and $R_{13}$ is hydrogen, and R''' denotes a radical identical to R' or a radical identical to R'' or Cl or one of the groups —S—$R_{15}$ or —P(O)(O$R_{17}$)$_2$, wherein $R_{15}$ is $C_1$–$C_{12}$ alkyl or a group

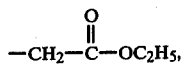

and $R_{17}$ is ethyl.

Examples of compounds of the general formulae are: 2-(3,5-di-tert.-butyl-4-hydroxyphenoxy)-4,6-bis-[(1,2,2,6,6-pentamethyl-piperidin-4-yl)-oxy]-1,3,5-triazine, 2-[3-(3-tert.-butyl-5-methyl-4-hydroxyphenyl)-propyl-N-methylamino]-4,6-bis-[(2,3,6-trimethyl-2,6-diethyl-piperidin-1-yl)-ethoxy]-1,3,5-triazine, 2-(3,5-di-tert.-butyl-4-hydroxyphenylthio)-4-[(2,3,6-trimethyl-2,6-diethylpiperidin-4-yl)-amino]-6-(diethylphosphonate)-1,3,5-triazine, 2,4-bis-(3-tert.-butyl-6-methyl-4-hydroxy-anilino)-6-[(2,2,6,6-tetramethylpiperidin-4-yl)-oxy]-1,3-pyrimidine, 2,4-bis-(3,5-di-tert.-butyl-4-hydroxyphenoxy)-6-[(2,3,6-trimethyl-2,6-diethylpiperidin-4-yl)-oxy]-1,3,5-triazine, 2-[3-(3-tert.-butyl-6-methyl-4-hydroxyphenyl)-propoxy]-4-[(1,2,2,6,6-pentamethylpiperidin-4-yl)-amino]-6-(n-octylthio)-1,3,5-triazine, 2-[3-(3,5-di-tert.-butyl-4-hydroxyphenyl)-2,2-dimethylpropylamino]-4-(n-dodecylthio)-6-[(2,3,6-trimethyl-2,4-diethylpiperidin-4-yl)-amino]-1,3,5-triazine, 2-(3-tert.-butyl-5-methyl-4-hydroxy-benzylamino)-4,6-bis-[(2,2,6,6-tetramethylpiperidin-1-yl)-ethyl-thio]-1,3,5-triazine, 2-[3-(3,5-di-tert.-butyl-4-hydroxyphenyl)-propylamino]-4-(n-octyl-thio)-6-[2,2,6,6-tetramethylpiperidin-4-yl)-amino]-1,3,5-triazine, 2-(3-tert.-butyl-5-methyl-4-hydroxyphenoxy)-4-[(2,2,6,6-tetramethylpiperidin-4-yl)-oxy]-6-(n-butylamino)-1,3,5-triazine, 2-(3,5-di-tert.-butyl-4-hydroxybenzyloxy)-4-[(N-acetyl-2,2,6,6-tetramethyl-piperidin-4-yl)-amino]-6-(azido)-1,3,5-triazine and 2-[2-(3-tert.-butyl-6-methyl-4-hydroxyphenyl)-ethylamino]-4-[(2,2,6,6-tetramethyl-4-hydroxypiperidin-1-yl)-ethoxy]-6-(ethoxy)-1,3,5-triazine.

The 1,3-pyrimidines and 1,3,5-triazines carrying mixed substituents can be manufactured by various methods which are in themselves known.

Usually, the starting material used is 2,4,6-trichloro-1,3,5-triazine of the formula

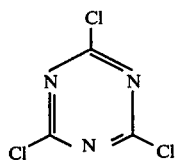

which is a known compound.

In order to attach a group R', R'' or R''' of the formula (II) to the heterocyclic base structure, about one mol of a compound of the formula VII is reacted with about one mol of a phenol of the formula

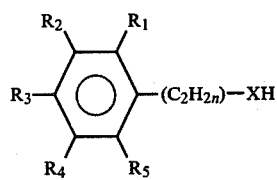

in the presence of a base and in a solvent.

Examples of suitable bases are organic nitrogen bases, such as triethylamine, pyridine or piperidine. Inorganic bases, such as alkali metal carbonates or alkali metal hydroxides, preferably sodium carbonate, are also suitable.

All protic and aprotic solvents which are sufficiently polar are suitable for use as solvents, such as, for example, acetone, acetone/water, methanol, ethanol, tetrahydrofurane or diethyl ether. Acetone, acetone/water, methanol or ethanol are preferentially used.

If two of the radicals R', R'' and R''' denote a group of the formula II, about one mol of a compound of the formula VII is reacted, in an analogous manner, with about two mols of the same phenol of the formula VIII or with one mol each of two different phenols of the formula VIII.

The groups of the formulae III, IV or V are linked to the heterocyclic system in the same way as described above for the phenolic radicals of the formula II.

Under the reaction conditions described above, a compound of the formula VII is reacted with one of the compounds

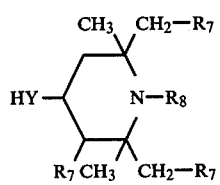

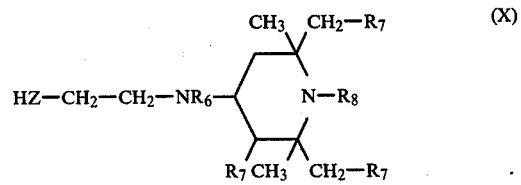

or

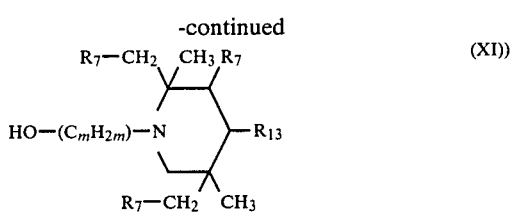

Advantageously, the phenolic component of the formula VIII is first allowed to react with the triazine or pyrimidine of the formula VII and the reaction with the piperidines of the formulae IX, X or XI is carried out subsequently.

The manufacture of the compounds of the formula I, wherein one of the radicals R', R" and R'" denotes the group —P(O)—(OR$_{17}$)$_2$, is effected by means of the known Arbusov reaction. Preferably, after the trichloride of the formula VII has been reacted with a phenol of the formula VIII and a piperidine of the formula IX, X or XI, the resulting monochloro compound is reacted with a phosphite of the formula P(OR$_{17}$)$_3$ in the presence of a salt, such as NiCl$_2$.6H$_2$O. The phosphite can here serve as the solvent at the same time.

The manufacture of the compounds of the formula I, in which one of the radicals R', R" and R'" denotes one of the groups —S—R$_{15}$, —O—R$_{17}$ or —NR$_{18}$R$_{19}$, is known and described, for example, in British Patent Specification No. 1,393,551. Here, an alkali metal mercaptide, an alkali metal phenolate or an amine of the formulae MS—R$_{15}$, MO—R$_{17}$ or HNR$_{18}$R$_{19}$ is reacted, preferably in a solvent. Preferably, an excess of the amine of the formula HNR$_{18}$R$_{19}$ is employed.

The compounds of the formula I, wherein one of the radicals R', R" and R'" denotes an azido group are manufactured by means of known substitution reactions.

Frequently, the substitution of the third chlorine atom of the compound of the formula VII cannot readily be effected and greatly depends on the nucleophilic character of the attacking group. The best results are achieved when this third reaction stage is carried out at an elevated temperature, preferably at reflux temperature.

The piperidines of the formulae IX and XI are known, for example 4-hydroxy-piperidines are known from DT-OS No. 2,352,658 and 4-amino-piperidines are known from U.S. Pat. No. 3,684,765. In general, the 4-OH compounds can be manufactured from the corresponding 4-oxopiperidines of the formula XII

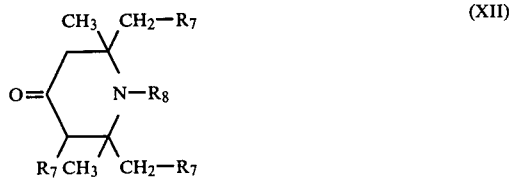

by reduction, for example by catalytic hydrogenation over Raney nickel, whilst the 4-NH$_2$ compounds are obtainable from a compound of the formula XII, for example, by means of a reductive conversion with ammonia.

The 4-oxopiperidines of the formula XII in which R$_8$ is hydrogen, can be manufactured by various processes.

Thus, for example, W. Traube in Chem. Ber. 41, 777 (1908) describes the reaction of an aliphatic ketone with ammonia.

4-Oxopiperidines of the formula XII in which R$_8$ denotes hydrogen, can also be manufactured analogously to the process described in U.S. Pat. No. 3,513,170. Here, an alkyl-substituted tetrahydropyrimidine is hydrolytically rearranged in the presence of an acid catalyst.

N-H compounds of the formula XII which carry different substituents in the 2-position and 6-position, can be manufactured by reacting a ketone of the formula CH$_3$—CO—CH$_2$—R$_7$ with ammonia. The pyrimidine formed is hydrolysed, as described in Helv. Chim. Acta 30, 114 (1947), to give an aminoketone of the formula XIII.

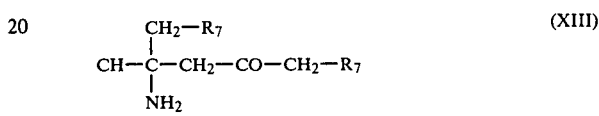

Compounds of the formula XIII are reacted, in a second process stage, with ammonia and a ketone CH$_3$—CO—CH$_2$—R$_7$, as is described, for example, in Monatsh. Chemie 88, 464 (1957). The compounds of the formula VII in which R$_8$ denotes hydrogen, can be obtained from the resulting pyrimidine by hydrolysis.

Compounds of the formula XII in which R$_8$ does not denote hydrogen, can be manufactured from the corresponding N-H compounds by substitution. This step involves the substitution reactions customary for secondary amines, although these reactions proceed more slowly because of the steric hindrance by the methyl group or the group —CH$_2$—R$_7$. For example, the N-H compounds can be reacted with alkyl, alkenyl, aralkyl or alkoxyalkyl halides, dialkyl sulphates, epichlorohydrins, esters of chlorocarboxylic acids, such as esters of chloroacetic acid, or acid chlorides or acid anhydrides.

The group —CH$_2$—CH(R$_{10}$)—OR$_{11}$ can be introduced by reacting with N-H-piperidines with an epoxide of the formula

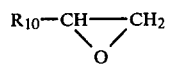

and subsequently acylating the product with an acyl chloride of the formula R$_{11}$Cl. The radical —(C$_m$H$_{2m}$)—OH is introduced analogously.

Compounds of the type of 2,2,6,6-tetramethyl-4-(carbalkoxycyanomethyl)-piperidine, which can be used as intermediate products, are moreover known from British Patent Specification No. 1,214,426.

Compounds of the formula XI in which R$_{13}$ denotes an ester grouping or amide grouping, are manufactured from 4-hydroxypiperidines or 4-aminopiperidines respectively by known methods of esterification.

Compounds of the formula X are, in principle, manufactured in an analogous manner. The introduction of the group —NR$_6$—CH$_2$—CH$_2$—ZH is described, for example, in DT-OS No. 2,349,962 and is effected by reacting the corresponding amine of the formula XIV

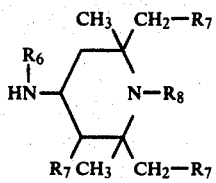

with a chloride of the formula XV

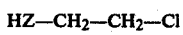

in the presence of an acid-binding agent.

According to the present invention, the compounds of the formula I can be used as stabilisers for plastics against damage thereto by the action of oxygen, heat and light. Examples of such plastics are the polymers listed in DT-OS No. 2,456,864 on pages 12–14.

The stabilisation of polyolefines, styrene polymers and polyurethanes is of particular importance and the compounds of the formula I are outstandingly suitable for this purpose. Examples of these are polyethylene of high and low density, polypropylene, ethylene/propylene copolymers, polystyrene, styrene/butadiene/acrylonitrile copolymers, mixtures of polyolefines or of styrene polymers, polyurethanes, based on polyethers or polyesters, in the form of films, fibres, lacquers, elastomers or foams. The compounds of the formula I are particularly suitable for stabilising ABS.

The stabilisers are added to the plastics in a concentration of 0.01 to 5% by weight, calculated on the material to be stabilised. Preferably 0.03 to 1.5, particularly preferably 0.2 to 0.6, % by weight of the compounds, calculated on the material to be stabilised, are incorporated into the latter.

The incorporation can be carried out after the polymerisation, for example by admixing the compounds and, optionally, further additives into the melt by the methods customary in the art, before or during shaping, or by applying the dissolved or dispersed compounds to the polymer, if appropriate with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added before crosslinking.

The invention thus also relates to the plastics which have been stabilised by the addition of 0.01 to 5% by weight of a compound of the formula I and which optionally can also contain further known and customary additives. The plastics stabilised in this way can be used in very diverse forms, for example as films, fibres, tapes, profiles or as binders for lacquers, adhesives or cements.

Examples which may be mentioned of further additives which can be employed together with the stabilisers to be used according to the invention are: antioxidants, such as simple 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, s-triazine compounds, amides of β-(3,5-di-tert.-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)propionic acid, esters of 3,5-di-tert.-butyl-4-hydroxyphenylacetic acid, acylaminophenols, benzyl-phosphonates and aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates, and furthermore nickel compounds, sterically hindered amines, oxalic acid diamides, metal deactivators, phosphites, compounds which destroy peroxides, polyamide stabilisers, basic co-stabilisers, PVC stabilisers, nucleating agents or other additives, such as, for example, plasticisers, lubricants, emulsifiers, fillers, carbon black, asbestos, kaolin, talc, glass fibres, pigments, optical brighteners, flameproofing agents and antistatic agents.

Examples of further additives which can be employed together with the stabilisers to be used according to the invention can be found in DT-OS No. 2,427,853 on pages 18–24.

The manufacture and use of the compounds according to the invention is described in more detail in the examples which follow.

EXAMPLE 1a 36.8 g of cyanuric chloride in 200 ml of boiling acetone were slowly poured into 400 ml of ice water, whilst stirring. The temperature was maintained between 0° and 5° C. by means of external cooling and 35.8 g of 4-amino-2-tert.-butyl-6-methylphenol and 21.2 g of sodium carbonate were added in the course of 30 minutes. Whilst stirring vigorously, the reaction mixture was kept at 8°–10° C. for one hour and then diluted with 200 ml of acetone. Stirring was continued for a further hour at 10° C. and the suspension was then poured into 2,000 ml of ice water. The precipitate was filtered off and dried in vacuo. The resulting 2-(3-tert.-butyl-5-methyl-4-hydroxyanilino)-4,6-dichloro-1,3,5-triazine has a melting point of 212° C.

EXAMPLE 1b 15.6 g of 4-amino-2,2,6,6-tetramethylpiperidine in 50 ml of acetone and 10.6 g of sodium carbonate in 50 ml of water were simultaneously added, at 25° C., to 32.7 g. of the product from Example 1a in 200 ml of acetone. The mixture was stirred for 3 hours at room temperature, the desired 2-(3-tert.-butyl-5-methyl-4-hydroxyanilino)-4-[(2,2,6,6-tetramethyl-piperidin-4-yl)-amino]-6-chloro-1,3,5-triazine precipitating. Recrystallisation from ethanol gave 31.5 g of dry product which melts at 240° C. (stabiliser No. 1).

EXAMPLE 2

1.15 g of sodium were dissolved in 150 ml of methanol and 7.3 g of n-octylmercaptan were added. A solution of 10.8 g of 2-(3-tert.-butyl-5-methyl-4-hydroxyanilino)-4-[(2,2,6,6-tetramethyl-piperidin-4-yl)-amino]-6-chloro-1,3,5-triazine in 200 ml of methanol was added to the resulting sodium n-octylmercaptide, whilst stirring. The reaction mixture was kept under reflux for 16 hours and then poured into 400 ml of ice water, a slightly brownish precipitate, which was filtered off, being formed. Recrystallization from ethyl acetate/hexane gives 13.9 g of almost colourless 2-(3-tert.-butyl-5-methyl-4-hydroxyanilino)-4-[(2,2,6,6-tetramethyl-piperidin-4-yl)-amino]-6-(n-octylthio)-1,3,5-triazine having a melting point of 133° C. (stabiliser 2).

EXAMPLE 3a 36.9 g of cyanuric chloride in 200 ml of boiling acetone were slowly poured into 400 ml of ice water, whilst stirring. The temperature was maintained between 0° and 5° C. by means of external cooling. 71.6 g of 4-amino-2-tert.-butyl-6-methylphenol in 100 ml of acetone and 42.4 g of sodium carbonate in 100 ml of water were simultaneously added at 10° C. The mixture was stirred at 10° C. for one hour and then at room temperature for 16 hours. The reaction mixture was then poured into ice water and the precipitate was filtered off and recrystallised from ethanol. In this way, it was possible to isolate 35.5 g of white 2,4-bis-(3-tert.-butyl-5-methyl-4-hydroxyanilino)-6-chloro-1,3,5-triazine which melts at 214° C.

EXAMPLE 3b 7.8 g of 4-amino-2,2,6,6-tetramethylpiperidine and then 5.06 g of triethylamine were added, at 25° C., to 23.5 g of 2,4-bis-(3-tert.-butyl-5-methyl-4-hydroxyanilino)-6-chloro-1,3,5-triazine dissolved in 500 ml of ethanol. The reaction mixture was kept at reflux temperature for 24 hours and was then cooled and poured into 300 ml of cold water. The resulting precipitate was filtered off, dried and recrystallised from ethyl acetate. The product thus isolated, that is to say 14.0 g of 2,4-bis-(3-t-butyl-5-methyl-4-hydroxyanilino)-6-[(2,2,6,6-tetramethyl-piperidin-4-yl)-amino]-1,3,5-triazine, melts at 164° C. (stabiliser No. 3).

EXAMPLE 4

6.25 g of 4-amino-2,2,6,6-tetramethyl-piperidine and 5.5 ml of triethylamine each in 50 ml of ethanol were simultaneously added in the course of one hour to 8.7 g of 2-[3-(3,5-di-t.-butyl-4-hydroxyphenyl)-2,2-dimethyl-propylamino]-4,6-dichlorotriazine in 100 ml of ethanol, and the reaction mixture was refluxed for 16 hours. The hot solution was subsequently poured into 100 ml of ice water. The precipitate was treated as in Example 3 and yielded 9.0 g of the white product, namely 2-[3-(3,5-di-t.-butyl-4-hydroxyphenyl)-2,2-dimethylpropylamino]-4,6-di-[(2,2,6,6-tetramethyl-piperidin-4-yl)-amino]-1,3,5-triazine, having a melting point of 120° C. (stabiliser No. 4).

EXAMPLE 5

A mixture of 5.6 g of 2-[3-(3,5-di-t.-butyl-4-hydroxyphenyl)-2,2-dimethylpropylamino]-4-[(2,2,6,6-tetramethyl-piperidin-4-yl)-amino]-6-chloro-1,3,5-triazine, 0.15 g of NiCl$_2$ 2H$_2$O and 300 ml of triethylphosphite was heated in a bomb tube for 8 hours at 180° C. The working-up method described in Example 1 gave 5.6 g of 2-[3-(3,5-di-t.-butyl-4-hydroxyphenyl)-2,2-dimethyl-propylamino]-4-[(2,2,6,6-tetramethyl-piperidin-4-yl)-amino]-6-(ethylphosphonate)-1,3,5-triazine (stabiliser No. 5), which is a viscous oil.

EXAMPLE 6

The sodium salt of n-decylthiol, which had been obtained by means of reaction of 1.15 g of sodium and 8.7 g of n-decylthiol in 50 ml of ethanol, was added dropwise to 14 g of 2-[3-(3,5-di-t.-butyl-4-hydroxyphenyl)-2,2-dimethyl-propylamino]-4-[(2,2,6,6-tetramethyl-piperidin-4-yl)-amino]-6-chloro-1,3,5-triazine in 300 ml of ethanol. After 1 hour of stirring at 24° C., the reaction mixture was refluxed for 16 hours. It was then cooled, the sodium chloride was filtered off and the solvent was evaporated off in vacuo. Recrystallisation from n-hexane/ethyl acetate yielded 6.4 g of the white 2-[3-(3,5-di-t.-butyl-4-hydroxyphenyl)-2,2-dimethyl-propylamino]-4-[(2,2,6,6-tetramethyl-piperidin-4-yl)-amino]-6-(n-decylthio)-1,3,5-triazine having a melting point of 50° C. (stabiliser No. 6).

EXAMPLE 7

In the same manner as in Example 6 was obtained 2-[2-(3,5-di-tert.-butyl-4-hydroxyphenyl)-2,2-dimethyl-ethylamino]-4-[(2,2,6,6-tetramethyl-piperidin-4-yl)-amino]-6-(n-octylthio)-1,3,5-triazine, m.p. 130° C. (stabiliser No. 7).

EXAMPLE 8

In the same manner as in Example 5 was obtained 2-[2-(3,5-di-t.-butyl-4-hydroxyphenyl)-2,2-dimethyl-ethylamino]-4-[(2,2,6,6-tetramethyl-piperidin-4-yl)-amino]-6-(ethylphosphonate)-1,3,5-triazine having a melting point of 250° C. (stabiliser No. 8).

EXAMPLE 9

In the same manner as in Example 6, the reaction of 2-(3-t-butyl-6-methyl-4-hydroxyanilino)-4-[(2,2,6,6-tetramethyl-piperidin-4-yl)-amino]-6-chloro-1,3,5-triazine and the sodium salt of n-octylthiol yielded the white test specimen, 2-(3-t-butyl-6-methyl-4-hydroxyanilino)-4-[(2,2,6,6-tetramethyl-piperidin-4-yl)-amino]-6-(n-octyl-thio)-1,3,5-triazine having a melting point of 90° C. (stabiliser No. 9).

EXAMPLE 10

The sodium salt from 0.01 mol of freshly produced sodium ethoxide and 1.8 g (0.01 mol) of (2,2,6,6-tetramethyl-piperidin-1-yl)-ethanol was added to a solution of 6.7 g of 2,4-di-[2-(3,5-di-t.-butyl-4-hydroxyphenyl)-2,2-dimethyl-ethylamino]-6-chloro-1,3,5-triazine in 50 ml of ethanol at 26° C. Refluxing for 16 hours and working up as in Example 3 yielded 4.9 g of 2,4-di-[2-(3,5-di-t.-butyl-4-hydroxyphenyl)-2,2-dimethyl-ethylamino]-6-[(2,2,6,6-tetramethyl-piperidin-1-yl)-ethoxy]-1,3,5-triazine having a melting point of 106° C. (stabiliser No. 10).

EXAMPLES 11 TO 19

The following stabilisers Nos. 11 to 19 were produced in a manner analogous to that in Example 3.

Table I

| Stabiliser | | M.P. |
|---|---|---|
| 11 | 2-(3-tert-butyl-5-methyl-4-hydroxyanilino)4,6-bis[(2,2,6,6-tetra-methyl-piperidin-4-yl)-amino]-1,3,5-triazine | 222° C. |
| 12 | 2-(3-tert-butyl-6-methyl-4-hydroxyanilino)4,6-bis[(2,2,6,6-tetra-methyl-piperidin-4-yl)-amino]-1,3,5-triazine | 200° C. |
| 13 | 2-(3,5-di-tert-butyl-4-hydroxyanilino)4,6-bis[(2,2,6,6-tetra-methyl-piperidin-4-yl)amino]-1,3,5-triazine | 156° C. |
| 14 | 2,4-bis(3-tert-butyl-6-methyl-4-hydroxyanilino)-6[2,2,6,6-tetra-methyl-piperidin-4-yl)-amino]-1,3,5-triazine | 280° C. |

Table I-continued

| Stabiliser | | M.P. |
|---|---|---|
| 15 | 2,4-bis(3,5-di-tert-butyl-4-hydroxy-benzyl)-6[(2,2,6,6-tetra-methyl-piperidin-4-yl)-amino]-1,3,5-triazine | 200° C. |
| 16 | 2,4-bis[2-(3,5-di-tert-butyl-4-hydroxy-phenyl)-2,2-dimethyl-ethylamino]-6-[bis(2,2,6,6-tetramethyl-piperidin-4-yl)-amino]-1,3,5-triazine | 130° C. |
| 17 | 2-(3,5-di-tert-butyl-4-hydroxyanilino)-4-[(2,2,6,6-tetramethyl-piperidin-4-yl)-amino]-6-(carbethoxymethylthio)-1,3,5-triazine | 120° C. |
| 18 | 2-(3,5-di-tert-butyl-4-hydroxyanilino)-4-[2-(2,2,6,6-tetra-methylpiperidin-4-yl-amino)-ethylthio]-6-(chloro)-1,3,5-triazine | 210° C. |
| 19 | 2-(3,5-di-tert-butyl-4-hydroxyanilino)-4,6-bis[2-(2,2,6,6-tetra-methyl-piperidin-4-yl-amino)-ethylthio-1,3,5-triazine | 120° C. |

EXAMPLE 20

100 parts of polypropylene (melt index 2.6 g/10 min., 230° C./2160 g) were thoroughly mixed in a shaking apparatus for 10 minutes with 0.2 part in each case of an additive given in the following Table II. The mixture obtained was kneaded at 200° C. for 10 minutes in a Brabender plastograph; the resulting mixture was subsequently pressed in a platen press at 260° C. platen temperature to form 1 mm thick sheets, from which were stamped strips 1 cm in width and 17 cm in length.

The testing of the effectiveness of the additives contained in the test strips was carried out by heat ageing in an air-circulation oven at 135° C. and 149° C., with a test strip containing no additive serving as a comparison. Three test strips from each formulation were used. The end point was defined as being that at which decomposition of the test strip commences, a condition easily recognisable by virtue of complete embrittlement. The results are given in days.

Table II

| Stabiliser No. | Days until start of decomposition at 135° C. | at 149° C. |
|---|---|---|
| without additive | 1 | <1 |
| 1 | 44 | 10 |
| 2 | 44 | 14 |
| 3 | 47 | 19 |
| 4 | 44 | 14 |
| 6 | 63 | 16 |
| 7 | 67 | 20 |
| 9 | 19 | 6 |
| 10 | 50 | 11 |
| 13 | 29 | 7 |
| 8 | 27 | 7 |

EXAMPLE 21

100 parts of polypropylene (melt index 2.6 g/10 minutes, 230° C./2160 g) were thoroughly mixed in a shaking apparatus with 0.1 part in each case of an additive listed in the following Table III and 0.3 part of dilaurylthiodipropionate, with the procedure being otherwise carried out as in Example 20. As a comparison specimen was used a test strip containing only 0.3 part of dilaurylthiodipropionate.

Table III

| Stabiliser No. | Days until start of decomposition at 135° C. | at 149° C. |
|---|---|---|
| without additive | 16 | 2 |
| 1 | 52 | 17 |
| 2 | 61 | 30 |
| 3 | 61 | 21 |
| 4 | 53 | 16 |
| 6 | | 21 |
| 7 | 56 | 20 |
| 9 | 24 | 8 |
| 10 | 52 | 13 |
| 13 | 24 | 7 |
| 8 | 38 | 17 |

EXAMPLE 22

A solution of in each case one of the stabilisers in Table IV, which consisted of 0.7 g of the stabiliser in 100 ml of cyclohexane, was worked into 100 g of unstabilised ABS powder. The cyclohexane was subsequently completely evaporated off in vacuo. To the dry ABS powder were then added 2% of titanium dioxide and 1% of ethylenediamino-bis-stearamide as lubricant, and mixed in for 12 hours in an automatic shaking machine. Processing was carried out on a two-roller mill at a roll temperature of 165° and 180° C. and at 16 and 18 r.p.m., respectively for 4 minutes. From the 0.8 mm thick sheet, pressed at 175° C. for 3 minutes, were stamped out specimens 4.5×1.7 cm in size and these were dried at 60° C. in vacuo for 4 hours.

The specimens produced in this manner were aged on an aluminium sheet in an air-circulation oven at 200° C. The ageing of the specimens was verified by means of the ATR technique. The increase of the carbonyl band at 1720 cm$^{-1}$ relative to the methylene band at 1455 cm$^{-1}$ was determined according to the base-line method.

As a measure for the protective action of the stabilisers tested was taken the time in minutes in which the intensity ratio of the carbonyl band at 1720 cm$^{-1}$ to the reference band at 1455 cm$^{-1}$ had risen to 0.1 (=T$_{0.1}$). The results are given in the following Table IV.

Table IV

| Stabiliser No. | T$_{0.1}$ in minutes |
|---|---|
| none | 5 |
| 1 | >60 |
| 2 | >60 |
| 3 | >60 |

What is claimed is:

1. A member selected from the group consisting of a compound of the formula I

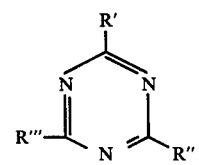

(I)

and an addition salt thereof, in which one of the radicals R', R" and R'" is a group of the formula II:

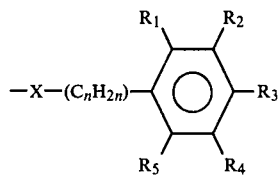

wherein one of $R_1$ and $R_3$ is —OH and the other is hydrogen, $R_2$ is $C_1$-$C_{12}$ alkyl, $C_5$-$C_7$ cycloalkyl, $C_6$-$C_{10}$ aryl or $C_7$-$C_9$ aralkyl, $R_4$ and $R_5$ are hydrogen, $C_1$-$C_{12}$ alkyl, $C_5$-$C_7$ cycloalkyl, $C_6$-$C_{10}$ aryl or $C_7$-$C_9$ aralkyl, n is an integer of 0 to 12 and X is —O—, —S— or —$NR_6$— wherein $R_6$ is hydrogen or $C_1$-$C_{12}$ alkyl, and one of the radicals R', R" and R'" is one of the groups

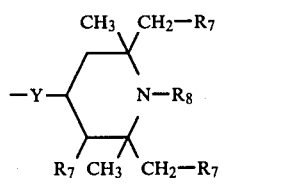

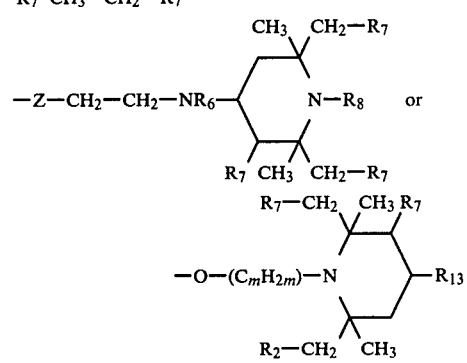

in which Y is —O— or —$NR_6$— wherein $R_6$ has the meaning defined above, Z is —O— or —S—, m is 1 to 6, $R_7$ is hydrogen or $C_1$-$C_8$ alkyl and $R_8$ is hydrogen, oxygen, $C_1$-$C_{12}$ alkyl, $C_3$-$C_6$ alkenyl, $C_3$-$C_4$ alkinyl, $C_2$-$C_{21}$ alkoxyalkyl, $C_7$-$C_8$ aralkyl, 2,3-epoxypropyl, an aliphatic acyl group with 1-4 C atoms or one of the groups —$CH_2COOR_9$, —$CH_2$—$CH(R_{10})$—$OR_{11}$, —$COOR_{12}$ or —$CONHR_{12}$, wherein $R_9$ is $C_1$-$C_{12}$ alkyl, $C_3$-$C_6$ alkenyl, phenyl, $C_7$-$C_8$ aralkyl or cyclohexyl, $R_{10}$ is hydrogen, methyl or phenyl, $R_{11}$ is hydrogen, an aliphatic, aromatic, araliphatic or alicyclic acyl group with 1-8 C atoms, wherein the aromatic part is unsubstituted or is substituted by chlorine, $C_1$-$C_4$ alkyl, $C_1$-$C_8$ alkoxy or by hydroxyl, and $R_{12}$ is $C_1$-$C_{12}$ alkyl, cyclohexyl, phenyl or benzyl, and $R_{13}$ is hydrogen, —OH or one of the groups —O—CO—$R_{14}$ or —N$R_{12}$—CO—$R_{14}$, wherein $R_{14}$ is $C_1$-$C_{12}$ alkyl or phenyl, and one of the radicals R', R" and R'" independently of the others is an identical or different group of the formula II, or is an identical or different group III, IV or V, or is —$N_3$, or one of the groups —S—$R_{15}$, —$OR_{17}$, —P(O)—$(OR_{17})_2$ or —$NR_{18}R_{10}$, wherein $R_{15}$ is hydrogen, $C_1$-$C_{18}$ alkyl, $C_5$-$C_7$ cycloalkyl, $C_6$-$C_{10}$ aryl, $C_7$-$C_9$ aralkyl or the group —$(C_pH_{2p})$—CO—$OR_{16}$ wherein $R_{16}$ is $C_1$-$C_{18}$ alkyl, and p is 1 to 6, $R_{17}$ is $C_1$-$C_{18}$ alkyl, $C_6$-$C_{10}$ aryl or $C_7$-$C_9$ aralkyl and $R_{18}$ and $R_{19}$ independently of one another are hydrogen, $C_1$-$C_{18}$ alkyl, $C_5$-$C_7$ cycloalkyl, $C_6$-$C_{10}$ aryl, $C_7$-$C_9$ aralkyl or the group

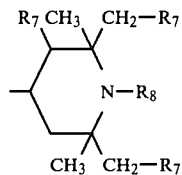

in which $R_7$ and $R_8$ have the meaning defined above.

2. A compound, according to claim 1, of the formula I in which one of the radicals R', R" and R'" is a group of the formula II wherein $R_1$ is hydrogen, $R_2$ is $C_1$-$C_{12}$ alkyl, $R_3$ is —OH, $R_4$ is hydrogen or $C_1$-$C_{12}$ alkyl, $R_5$ is hydrogen or $C_1$-$C_6$ alkyl, n is 0 to 6 and X is —O—, —S— or —$NR_6$— wherein $R_6$ is hydrogen or $C_1$-$C_4$ alkyl, and one of the radicals R', R" and R'" is one of the groups of the formula III or V, in which m is 2, Y is —O— or —$NR_6$—, $R_7$ is hydrogen or $C_1$-$C_4$ alkyl and $R_8$ is hydrogen, oxygen, $C_1$-$C_8$ alkyl, $C_3$-$C_4$ alkenyl or alkinyl, $C_2$-$C_6$ alkoxyalkyl, $C_7$-$C_8$ aralkyl, acetyl, acryloyl or crotonoyl or one of the groups —$CH_2$—$COOR_9$, —$CH_2$—$CH(R_{10})$—$OR_{11}$, —$COOR_{12}$ or —$CONHR_{12}$, wherein $R_9$ is $C_1$-$C_4$ alkyl, $C_3$-$C_4$ alkenyl, phenyl, $C_7$-$C_8$ aralkyl or cyclohexyl, $R_{10}$ is hydrogen, methyl or phenyl, $R_{11}$ is hydrogen or an aliphatic, aromatic, alicyclic or araliphatic acyl group with 1-18 C atoms, wherein the aromatic part is unsubstituted or is substituted by chlorine, $C_1$-$C_4$ alkyl, $C_1$-$C_8$ alkoxy or hydroxyl, $R_{12}$ is $C_1$-$C_{12}$ alkyl and $R_{13}$ is hydrogen, —OH or one of the groups —O—CO—$R_{14}$ or —NH—CO—$R_{14}$, wherein $R_{14}$ is $C_1$-$C_{12}$ alkyl, and one of the radicals R', R" and R'" independently of the others is an identical or different group of the formula II, wherein the substituents have the meaning defined above, or is an identical or different group III or V, wherein the substituents have the meaning defined above, or is —$N_3$ or Cl or one of the groups —S—$R_{15}$, —$OR_{17}$, —P(O)—$(OR_{17})_2$ or —$NR_{18}R_{19}$, wherein $R_{15}$ is hydrogen, $C_1$-$C_{18}$ alkyl or the group —$(C_pH_{2-p})$—CO—$OR_{16}$ wherein $R_{16}$ is $C_1$-$C_{18}$ alkyl and p is 1 to 4, $R_{17}$ is $C_1$-$C_{12}$ alkyl and $R_{18}$ and $R_{19}$ independently of one another are hydrogen, $C_1$-$C_{12}$ alkyl, phenyl or a group of the formula VI.

3. A compound according to claim 1, of the formula I in which R' is a group of the formula II wherein $R_1$ is hydrogen, $R_2$ is $C_1$-$C_8$ alkyl, $R_3$ is —OH, $R_4$ is hydrogen or $C_1$-$C_4$ alkyl, $R_5$ is hydrogen or methyl, n is 0 to 5 and X is —NH—, and R" is one of the groups of the formula III or V, wherein m is 2, Y is —NH—, $R_7$ is hydrogen or methyl and $R_8$ is hydrogen, $C_1$-$C_4$ alkyl or acetyl, and $R_{13}$ is hydrogen or —OH, and R'" is identical to or different from R' and is a group of the formula II in which the substituents have the meaning defined above or R'" is identical to or different from R" and is one of the groups III or V in which the substituents have the meaning defined above, or is —$N_3$ or one of the radicals —S—$R_{15}$, —$O$—$R_{17}$, —P(O)—$(OR_{17})_2$ or —$NHR_{19}$, wherein $R_{15}$ is $C_1$-$C_{12}$ alkyl or the group —$(C_pH_{2-p})$—CO—$OR_{16}$ wherein $R_{16}$ is $C_1$-$C_2$ alkyl and n is 1 or 2, $R_{17}$ is $C_1$-$C_2$ alkyl and $R_{19}$ is a group of the formula VI.

4. A compound, according to claim 1, of the formula I in which R' is a group of the formula II wherein $R_1$ is hydrogen, $R_2$ is $C_1$-$C_4$ alkyl, $R_3$ is —OH, $R_4$ is hydrogen or $C_1$-$C_4$ alkyl, $R_5$ is hydrogen or methyl, n is 0 to 5 and X is —NH—, and R" is one of the groups of the formula III or V wherein Y is —NH—, m is 2, $R_7$ is hydrogen, $R_8$ is hydrogen, and $R_{13}$ is hydrogen, and R''' is a radical identical to R' or a radical identical to R" or Cl or one of the groups —S—$R_{15}$ or —P(O)(O$R_{17}$)$_2$, wherein $R_{15}$ is hydrogen or $C_1$-$C_{12}$ alkyl or a group

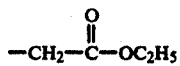

and $R_{17}$ is $C_2$-$C_4$ alkyl.

5. A compound, according to claim 1, of the formula I in which R' and R" have the meaning defined in claim 4 and R''' is the same radical as the group R' or the group R".

6. A compound 2,4-di-(3-t.-butyl-5-methyl-4-hydroxyanilino)-6-[(2,2,6,6-tetramethyl-piperidin-4-yl)-amino]-1,3,5-triazine, according to claim 1.

7. 2-[2-(3,5-di-t.-Butyl-4-hydroxyphenyl)]-2,2-dimethylethylanilino-4-[(2,2,6,6-tetramethyl-piperidin-4-yl)-amino]-6-(n-octylthio)-1,3,5-triazine, according to claim 1.

8. 2-[3-(3,5-di-t.-Butyl-4-hydroxyphenyl)-2,2-dimethylpropylamino]-4-[(2,2,6,6-tetramethyl-piperidin-4-yl)-amino]-6-(n-decylthio)-1,3,5-triazine, according to claim 1.

9. 2-[3-(3,5-di-t.-Butyl-4-hydroxyphenyl)-2,2-dimethylpropylamino]-4,6-di-[(2,2,6,6-tetramethylpiperidin-4-yl)-amino]1,3,5-triazine, according to claim 1.

* * * * *